(12) United States Patent
Dickason et al.

(10) Patent No.: US 7,795,246 B2
(45) Date of Patent: *Sep. 14, 2010

(54) PARTICLE-FORMING COMPOSITIONS CONTAINING FUSED PYRROLOCARBAZOLES

(75) Inventors: Dave Dickason, Cincinnati, OH (US); Bradley T. McIntyre, Thorndale, PA (US); Piyush R. Patel, Wallingford, PA (US)

(73) Assignee: Cephalon, Inc., Frazer, PA (US)

( * ) Notice: Subject to any disclaimer, the term of this patent is extended or adjusted under 35 U.S.C. 154(b) by 1765 days.

This patent is subject to a terminal disclaimer.

(21) Appl. No.: 10/718,077

(22) Filed: Nov. 20, 2003

(65) Prior Publication Data

US 2004/0220176 A1  Nov. 4, 2004

Related U.S. Application Data

(60) Continuation-in-part of application No. 09/698,901, filed on Oct. 27, 2000, now Pat. No. 6,660,729, which is a division of application No. 09/368,409, filed on Aug. 5, 1999, now Pat. No. 6,200,968.

(60) Provisional application No. 60/095,611, filed on Aug. 6, 1998.

(51) Int. Cl.
*A61K 31/55* (2006.01)
*A61K 31/553* (2006.01)
*C07D 273/00* (2006.01)

(52) U.S. Cl. .......................... 514/211.08; 514/211.1; 514/211.09; 514/212.01; 514/724; 540/545

(58) Field of Classification Search .................. 514/724
See application file for complete search history.

(56) References Cited

U.S. PATENT DOCUMENTS

| | | | |
|---|---|---|---|
| 4,877,776 A | 10/1989 | Murkata et al. | |
| 4,923,986 A | 5/1990 | Murkata et al. | |
| 5,043,335 A | 8/1991 | Kleinschrothe et al. | |
| 5,093,330 A | 3/1992 | Caravatti et al. | |
| 5,242,932 A | 9/1993 | Gandy et al. | |
| 5,461,146 A | 10/1995 | Lewis et al. | |
| 5,468,872 A | 11/1995 | Glicksman et al. | |
| 5,475,110 A | 12/1995 | Hudkins et al. | |
| 5,516,771 A | 5/1996 | Dionne et al. | |
| 5,591,855 A | 1/1997 | Hudkins et al. | |
| 5,594,009 A | 1/1997 | Hudkins et al. | |
| 5,599,808 A | 2/1997 | Goldstein et al. | |
| 5,616,724 A | 4/1997 | Hudkins et al. | |
| 5,621,100 A | 4/1997 | Lewis et al. | |
| 5,621,101 A | 4/1997 | Lewis et al. | |
| 5,658,898 A | 8/1997 | Weder et al. | |
| 5,705,511 A | 1/1998 | Hudkins et al. | |
| 5,726,164 A | 3/1998 | Weder et al. | |
| 5,801,190 A | 9/1998 | Hudkins et al. | |
| 6,200,968 B1 | 3/2001 | Dickason et al. | |
| 6,660,729 B1 * | 12/2003 | Dickason et al. | 514/211.09 |

FOREIGN PATENT DOCUMENTS

| | | | |
|---|---|---|---|
| EP | 0 303 697 | | 2/1989 |
| EP | 0 323 171 | | 7/1989 |
| EP | 0 657 164 | | 6/1995 |
| EP | 0 850 646 | | 7/1998 |
| JP | 62-120388 | | 6/1987 |
| JP | 62-155284 | | 7/1987 |
| JP | 62-155285 | | 7/1987 |
| JP | 63-295588 | | 12/1988 |
| JP | 63-295589 | | 12/1988 |
| JP | 04-124122 | | 4/1992 |
| WO | WO88/07045 | * | 9/1988 |
| WO | WO 93/00909 | | 1/1993 |
| WO | WO 93/08809 | | 5/1993 |
| WO | WO 97/46565 | | 12/1997 |
| WO | WO 00/48571 | | 8/2000 |
| WO | WO00/48571 | * | 8/2000 |

OTHER PUBLICATIONS

Berg et al., "K-252a Inhibitis Nerve Growth Factor-induced trk Proto-oncogene Tyrosine Phosphorylation and Kinase Activity", J. Biol. Chem., 1992, 267, pp. 13-16.
Kase et al., "K-252 Compounds, Novel and Potent Inhibitors of Protein Kinase C and Cyclic Nucleotide-Dependent Protein Kinases", Biochem, Biophys. Res. Commun., 1987, 142, pp. 436-440.
Moody et al., "Synthesis of the Staurosporine Aglycon", J. Org. Chem., 1992, 57, pp. 2105-2114.
Nakanish et al., "K-252b, c and d, Potent Inhibitors of Protein Kinase C from Microbial Origin", J. Antibiotices, 1986, 34, pp. 1066-1071.
Shah et al., "Self-emulsifying drug delivery systems (SEDDS) with polyglycolyzed glycerides for improving in vitro dissolution and oral absorption of lipophilic drugs", International Journal of Pharmaceutics (Netherlands), 1994, 106, pp. 15-23.
Yamamoto et al., "Enhanced rectal absorption of itazigrel formulated with polysorbate 80 micelle vehicle in rat: role of co-administered esterase", J. Pharm. Pharmacol., 1994, 46, pp. 608-611.
Nomak et al., Tetrahedron Letters 42 (2001) 7929-7933.
Levis et al., "A FLT3-targeted tyrosine kinase inhibitors is cytotoxic to leukemia cells in vitro and vivo," BLOOD, Jun. 2002, vol. 99, No. 11, 3885-3891.

* cited by examiner

*Primary Examiner*—Yong S Chong
*Assistant Examiner*—Jody L Karol

(57) ABSTRACT

A non-aqueous, particle-forming, fused pyrrolocarbazole-containing composition is disclosed. Upon contact with an aqueous medium, the particle-forming composition spontaneously disperses into suspended particles, thereby forming a stable suspension that provides greatly improved bioavailability of orally administered fused pyrrolocarbazole compounds.

21 Claims, No Drawings

PARTICLE-FORMING COMPOSITIONS CONTAINING FUSED PYRROLOCARBAZOLES

This application is a continuation-in-part of U.S. application Ser. No. 09/698,901, filed Oct. 27, 2000, now U.S. Pat. No. 6,660,729, which is a division of U.S. application Ser. No. 09/368,409, filed Aug. 5, 1999, now U.S. Pat. No. 6,200,968, which claims priority to U.S. provisional application No. 60/095,611 filed Aug. 6, 1998.

FIELD OF THE INVENTION

The invention relates to non-aqueous, particle-forming pharmaceutical compositions containing fused pyrrolocarbazoles or derivatives thereof. The invention is also directed to stable solutions which result upon contacting the particle-forming compositions of the present invention with an aqueous medium. The invention is further directed to methods of medical treatment which include treatment of a subject with the compositions or solutions of the present invention.

BACKGROUND OF THE INVENTION

Fused pyrrolocarbazoles display various pharmacological activities. For example, fused pyrrolocarbazoles are useful for treatment of neurological diseases or disorders, and some display antifungal, antimicrobial, or antitumor activity. In some cases this is accomplished by modulation of neurotrophic responses through effects on protein kinase activity (Berg et al., *J. Biol. Chem.* 267:13-16 (1992)). Fused carbazoles and their derivatives have been isolated from a various microorganisms, including *S. staurosporeus, N. aerocoligenes, Actinomadura* and *Nocardiopsis* sp, (Kase et al., *Biochem. Biophys. Res. Commun.* 142: 436-440, (1987)).

Specific fused pyrrolocarbazoles, such as indolocarbazoles, which have been characterized include the following: staurosporine and rebeccamycin (Moody et al., supra); K-252a, K-252b (Kase et al., supra); K-252c (also called staurosporine aglycon) (Moody et al., supra), K-252d and derivatives thereof (published Japanese patent applications 60-257652, 60-295172, 62-327858, 62-327859, and 60-295173). K-252a, K-252b, K-252c, and K-252d are insoluble in water (Nakanishi et al., *J. Antibodies,* 34:1066, (1986)).

In general, fused pyrrolocarbazoles display very low water solubility. Dry pharmaceutical preparations (dragees, tablets and capsules) of staurosporine derivatives that may contain polyethylene glycol and polyvinylpyrrolidone have been described in U.S. Pat. No. 5,093,330. Conventional pharmaceutical formulations that include indolocarbazoles are described in U.S. Pat. No. 5,043,335 and PCT publication No. WO 93/00909. Aqueous indolocarbazole compositions are described in U.S. Pat. No. 5,599,808.

Self-emulsifying drug delivery systems ("SEDDS") have been developed for drugs that display very low water solubility but good oil solubility. See, e.g., Shah et al., *International Journal of Pharmaceutics* (*Netherlands*) 106:15-23, (1994). Despite their low water solubility, fused carbazoles are generally unsuited for SEDDS because of their low oil solubility.

SUMMARY OF THE INVENTION

Accordingly, one object of the present invention is to provide particle-forming compositions containing fused pyrrolocarbazoles or derivatives thereof. Particularly, the compositions of the present invention are non-aqueous and contain an amount of surfactant sufficient to make a fused pyrrolocarbazole or a derivative thereof particle-forming.

It is another object of the invention to provide a stable suspension that comprises suspended fused pyrrolocarbazole-containing particles that greatly improves bioavailability upon oral administration.

It is another object of the invention to provide a method of forming a stable suspension of fused pyrrolocarbazole-containing particles which comprises contacting the particle-forming compositions of the present invention with an aqueous medium.

It is another object of the invention to provide a method of treating a disease or disorder in a mammal which comprises administering a therapeutically effective amount of the particle-forming compositions of the present invention.

These and other objects, which will become apparent during the following detailed description, have been achieved by the inventor's discovery that fused pyrrolocarbazoles and derivatives thereof can be formulated with suitable concentrations of one or more surfactants to make a non-aqueous, particle-forming composition, wherein the composition spontaneously disperses into suspended particles upon contact with an aqueous medium.

DETAILED DESCRIPTION OF THE INVENTION

Thus, in a first embodiment, the present invention provides a non-aqueous, particle-forming composition comprising a fused pyrrolocarbazole and a surfactant. In a preferred embodiment, the fused pyrrolocarbazole has Formula I:

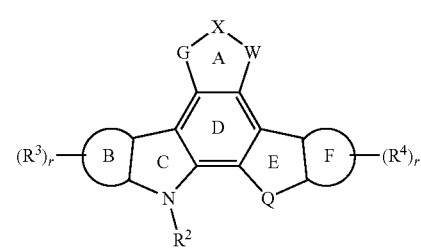

or a stereoisomer or pharmaceutically acceptable salt form thereof, wherein:

ring B and ring F, are independently selected from:
  a) an unsaturated 6-membered carbocyclic aromatic ring in which from 1 to 3 carbon atoms may be replaced by nitrogen atoms;
  b) an unsaturated 5-membered carbocyclic aromatic ring; and
  c) an unsaturated 5-membered carbocyclic aromatic ring in which either:
    1) one carbon atom is replaced with an oxygen, nitrogen, or sulfur;
    2) two carbon atoms are replaced with a sulfur and a nitrogen, an oxygen and a nitrogen, or two nitrogens; or
    3) three carbon atoms are replaced with three nitrogens;

G—X—W is selected from:
  a) —($Z^1Z^2$)C—N($R^1$)—C($Z^1Z^2$)—;
  b) —CH($R^1$)—C(=O)—N($R^1$)—; and
  c) —N($R^1$)—C(=O)—CH($R^1$)—;

$Z^1$ and $Z^2$, at each occurrence, are independently selected from H, H; H, OR; H, SR; H, N(R)$_2$; and a group wherein $Z^1$ and $Z^2$ together form a moiety selected from =O, =S, and =NR; with the proviso that at least one of the pairs $Z^1$ and $Z^2$ form =O;

R is selected from H, substituted or unsubstituted alkyl having from 1 to 6 carbons, OH, alkoxy having from 1 to 4 carbons, $OC(=O)R^{1a}$, $OC(=O)NR^{1c}R^{1d}$, $O(CH_2)_p NR^{1c}R^{1d}$, $O(CH_2)_p OR^{1b}$, substituted or unsubstituted arylalkyl having from 6 to 10 carbons, and substituted or unsubstituted heteroarylalkyl;

$R^1$ is selected independently from:
 a) H, substituted or unsubstituted alkyl having from 1 to 6 carbons, substituted or unsubstituted aryl, substituted or unsubstituted arylalkyl, substituted or unsubstituted heteroaryl, and substituted or unsubstituted heteroarylalkyl;
 b) $C(=O)R^{1a}$;
 c) $OR^{1b}$;
 d) $C(=O)NHR^{1b}$, $NR^{1c}R^{1d}$, $(CH_2)_p NR^{1c}R^{1d}$, $(CH_2)_p OR^{1b}$, $O(CH_2)_p OR^{1b}$ and $O(CH_2)_p NR^{1c}R^{1d}$;

$R^{1a}$ is selected from substituted or unsubstituted alkyl, substituted or unsubstituted aryl and heteroaryl;

$R^{1b}$ is selected from H and substituted or unsubstituted alkyl having from 1 to 6 carbons;

$R^{1c}$ and $R^{1d}$ are each independently selected from H, substituted or unsubstituted alkyl having from 1 to 4 carbons, and a linking group of the formula —$(CH_2)_2$—$X^1$—$(CH_2)_2$—;

$X^1$ is selected from —O—, —S—, and —$CH_2$—;

$R^2$ is selected from H, $SO_2R^{2a}$, $CO_2R^{2a}$, $C(=O)R^{2a}$, $C(=O)NR^{2c}R^{2d}$, and alkyl of 1-8 carbons, alkenyl of 2-8 carbons, alkynyl of 2-8 carbons, wherein:
 1) each alkyl, alkenyl, and alkynyl is unsubstituted; or
 2) each alkyl, alkenyl, and alkynyl is substituted with 1-3 $R^5$;

$R^{2a}$ is selected from alkyl of 1 to 6 carbons, aryl, $OR^{2b}$, $CONH_2$, $NR^{2c}R^{2d}$, $(CH_2)_p NR^{2c}R^{2d}$, and $O(CH_2)_p NR^{2c}R^{2d}$;

$R^{2b}$ is selected from H and substituted or unsubstituted alkyl having from 1 to 6 carbons;

$R^{2c}$ and $R^{2d}$ are each independently selected from H, substituted or unsubstituted alkyl having from 1 to 6 carbons, and a linking group of the formula —$(CH_2)_2$—$X^1$—$(CH_2)_2$—;

$R^3$ and $R^4$, at each occurrence, are independently selected from:
 a) H, aryl, heteroaryl, F, Cl, Br, I, CN, $CF_3$, $NO_2$, OH, $OR^9$, $O(CH_2)_p NR^{11}R^{12}$, $OC(=O)R^9$, $OC(=O)NR^{11}R^{12}$, $O(CH_2)_p OR^{10}$, $CH_2OR^{10}$, $NR^{11}R^{12}$, $NR^{10}S(=O)_2R^9$, and $NR^{10}C(=O)R^9$;
 b) $CH_2R^{14}$;
 c) $NR^{10}C(=O)NR^{11}R^{12}$, $CO_2R^{10}$, $C(=O)R^9$, $C(=O)NR^{11}R^{12}$, $CH=NOR^{10}$, $CH=NR^{10}$, $(CH_2)_p NR^{11}R^{12}$, $(CH_2)_p NHR^{14}$, and $CH=NNR^{11}R^{12}$;
 d) $S(O)_y R^9$, $(CH_2)_p S(O)_y R^9$, $CH_2 S(O)_y R^{14}$;
 e) alkyl having from 1 to 8 carbons, alkenyl having from 2 to 8 carbons, and alkynyl having 2 to 8 carbons, wherein
  1) each alkyl, alkenyl, or alkynyl group is unsubstituted; or
  2) each alkyl, alkenyl, or alkynyl group is substituted with 1 to 3 $R^5$;

$R^5$ is selected from aryl having from 6 to 10 carbons, heteroaryl, arylalkoxy, heterocycloalkoxy, hydroxyalkoxy, alkyloxy-alkoxy, hydroxyalkylthio, alkoxy-alkylthio, F, Cl, Br, I, CN, $NO_2$, OH, $OR^9$, $X^2(CH_2)_p NR^{11}R^{12}$, $X^2(CH_2)_p C(=O)NR^{11}R^{12}$, $X^2(CH_2)_p OC(=O)NR^{11}R^{12}$, $X^2(CH_2)_p CO_2R^9$, $X^2(CH_2)_p S(O)_y R^9$, $X^2(CH_2)_p NR^{10}C(=O)NR^{11}R^{12}$, $OC(=O)R^9$, $OC(=O)NHR^{10}$, O-tetrahydropyranyl, $NR^{11}R^{12}$, $NR^{10}C(=O)R^9$, $NR^{10}CO_2R^9$, $NR^{10}C(=O)NR^{11}R^{12}$, $NHC(=NH)NH_2$, $NR^{10}S(O)_2R^9$, $S(O)_y R^9$, $CO_2R^{10}$, $C(=O)NR^{11}R^{12}$, $C(=O)R^9$, $CH_2OR^{10}$, $CH=NNR^{11}R^{12}$, $CH=NOR^{10}$, $CH=NR^9$, $CH=NNHCH(N=NH)NH_2$, $S(=O)_2 NR^{11}R^{12}$, $P(=O)(OR^{10})_2$, $OR^{14}$, and a monosaccharide having from 5 to 7 carbons wherein each hydroxyl group of the monosaccharide is independently either unsubstituted or is replaced by H, alkyl having from 1 to 4 carbons, alkylcarbonyloxy having from 2 to 5 carbons, or alkoxy having from of 1 to 4 carbons;

$X^2$ is O, S, or $NR^{10}$;

Q is selected from:
 1) $NR^6$;
 2) an unsubstituted alkylene of 1-3 carbons;
 3) a substituted alkylene of 1-3 carbons;
 4) CH=CH, CH(OH)CH(OH), O, S, $S(=O)$, $S(=O)_2$, $C(=O)$, $C(=NOR^{11})$, $C(OR^{11})(R^{11})$, $C(=O)CH(R^{13})$, $CH(R^{13})C(=O)$, $C(R^{10})_2$, $C(=NOR^{11})CH(R^{13})$, $CH(R^{13})C(=NOR^{11})$, $CH_2Z$, Z—$CH_2$, $CH_2ZCH_2$;

Z is selected from $C(R^{11})(OR^{11})$, O, S, $C(=O)$, $C(=NOR^{11})$, and $NR^{11}$;

$R^6$ is selected from H, $SO_2R^{2a}$, $CO_2R^{2a}$, $C(=O)R^{2a}$, $C(=O)NR^{1c}R^{1d}$, and alkyl of 1-8 carbons, alkenyl of 2-8 carbons, alkynyl of 2-8 carbons, wherein:
 1) each alkyl, alkenyl, and alkynyl is unsubstituted;
 2) each alkyl, alkenyl, and alkynyl is substituted with 1-3 $R^5$; or alternatively, when Q is $NR^6$ or $C(R^{10})_2$, $R^6$ or one $R^{10}$ joins with $R^2$ to form:

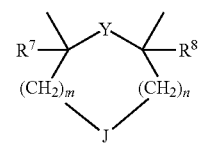

wherein $R^7$ and $R^8$ are each independently selected from H, OH, alkyl having from 1 to 6 carbons, alkoxy having from 1 to 6 carbons, substituted or unsubstituted arylalkyl having from 6 to 10 carbons, substituted or unsubstituted heteroarylalkyl, $(CH_2)_p OR^{10}$, $(CH_2)_p OC(=O)NR^{11}R^{12}$, and $(CH_2)_g NR^{11}R^{12}$; or $R^7$ and $R^8$ together form a linking group of the formula $CH_2$—$X^3$—$CH_2$;

$X^3$ is a bond, O, S, or $NR^{10}$;

$R^9$ is selected from alkyl having 1 to 6 carbons, $(CH_2)_r$aryl and $(CH_2)_r$heteroaryl;

$R^{10}$ is selected from H, alkyl having from 1 to 6 carbons, $(CH_2)_r$aryl and $(CH_2)_r$heteroaryl;

$R^{11}$ and $R^{12}$, at each occurrence, are independently selected from:
 1) H and substituted or unsubstituted alkyl having from 1 to 6 carbons; or
 2) $R^{11}$ and $R^{12}$ together form —$(CH_2)_2$—$X^1$—$(CH_2)_2$—;

Y is selected from O, S, $N(R^{10})$, $N^+(O^-)(R^{10})$, $N(OR^{10})$, and $CH_2$;

J is selected from the group consisting of a bond, O, CH=CH, S, $C(=O)$, $CH(OR^{10})$, $N(R^{10})$, $N(OR^{10})$, $CH(NR^{11}R^{12})$, $C(=O)N(R^{17})$, $N(R^{17})C(=O)$, $N(S(O)_y R^9)$, $N(S(O)_y NR^{11}R^{12})$, $N(C(=O)R^{17})$, $C(R^{15}R^{16})$, $N^+(O^-)(R^{10})$, CH(OH)CH(OH), and $CH(O(C=O)R^9)CH(OC(=O)R^9)$;

$R^{13}$ is selected from alkyl having from 1 to 4 carbons, aryl, and arylalkyl having from 7 to 14 carbons;

$R^{14}$ is the residue of an amino acid after the hydroxyl group of the carboxyl group is removed;

$R^{15}$ and $R^{16}$, at each occurrence is selected from H, OH, C(=O)$R^{10}$, O(C=O)$R^9$, alkyl-OH, and $CO_2R^{10}$;

$R^{17}$ is selected from the group consisting of H, alkyl, aryl, and heteroaryl;

m and n are independently selected from 0, 1, and 2;

p is independently selected from 1, 2, 3, and 4;

r is independently selected from 0, 1, and 2; and y is independently selected from 0, 1 and 2.

In certain preferred embodiments, rings B and F are phenyl. In other preferred embodiments, G-X—W is selected from $CH_2NR^1C$(=O), C(=O)$NR^1CH_2$, and C(=O)$NR^1C$(=O). In other preferred embodiments, Q is $NR^6$.

In other preferred embodiments, the fused pyrrolocarbazole has the Formula II-a:

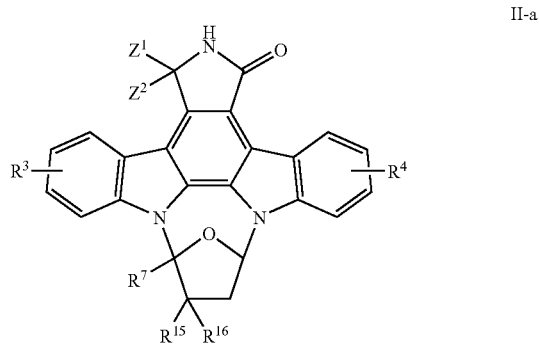

II-a

In certain more preferred embodiments, $Z^1$ and $Z^2$ are H, $R^3$ and $R^4$ are selected from H, alkyl, Cl, Br, $CH_2OH$, $CH_2SOCH_2CH_3$, $CH_2SO_2CH_2CH_3$, $NHCONHC_6H_5$, $CH_2SCH_2CH_3$, $CH_2SC_6H_5$, $NHCO_2CH_3$, $CH_2OC$(=O)$NHCH_2CH_3$, $N(CH_3)_2$, CH=NNH, $CH_2N(CH_3)_2$, $CH_2OCH_2CH_3$, $R^7$ is selected from H and alkyl, and $R^{15}$ and $R^{16}$ are independently selected from H, alkyl, OH, $CH_2OH$, alkoxy, and $CO_2$alkyl. In certain even more preferred embodiments, the fused carbazoles are indolocarbazoles as set forth in Tables 1-A and 1-B.

In certain preferred embodiments, the particle-forming composition further comprises one or more of an organic solvent, a lipid, or an antioxidant. In certain preferred embodiments, the amount of surfactant is at least about 20% (w/w). In certain more preferred embodiments, the amount of surfactant is at least 40% about (w/w). In certain more preferred embodiments, the amount of surfactant is at least about 50% (w/w).

In certain preferred embodiments, the surfactant is selected from polyethylene glycol stearate, d-α-tocopheryl polyethylene glycol succinate, polyoxyl stearate, polyoxyl castor oil, a polyoxyethylene sorbitan fatty acid ester, a polyethylene glycol ether, a saturated polyglycolized glyceride, a fatty acid ester of polyethylene glycol, a hydroxylated lecithin, a medium chain monoglyceride, a medium chain fatty acid ester, and polyethylene-propylene glycol copolymer. In other preferred embodiments, the lipid is a diester of coconut fatty acids and propylene glycol. In other preferred embodiments, the organic solvent is selected from propylene glycol, propylene carbonate, dimethyl isosorbide, and polyethylene glycol (PEG). In other preferred embodiments, the antioxidant is selected from ascorbic acid, a fatty acid ester of ascorbic acid, and butylated hydroxyanisole.

In certain preferred embodiments, the fused pyrrolocarbazole is present at a concentration of about 1 to about 300 mg/ml. In certain more preferred embodiments, the fused pyrrolocarbazole is present at a concentration of about 1 to about 100 mg/ml. In certain further more preferred embodiments, the concentration is about 1 to about 50 mg/ml.

In certain embodiments, the composition is a semi-solid or solid at room temperature. In certain more preferred embodiments, the semi-solid or solid is in the form of a capsule or tablet.

In another embodiment, the present invention provides a stable suspension of fused pyrrolocarbazole-containing particles in an aqueous suspension medium. In certain preferred embodiments, the particles have a diameter less than about 400 nm. In certain more preferred embodiments, the particles have a diameter less than about 100 nm.

In another embodiment, the present invention provides a method of forming a stable suspension of fused pyrrolocarbazole-containing, suspended particles, comprising contacting a fused pyrrolocarbazole in a non-aqueous liquid containing a surfactant in an amount from about 20% to greater than 99% with an aqueous medium. In a preferred method the particle-forming composition is contacted with an aqueous medium in vitro. In another preferred method, the particle-forming composition is contacted with an aqueous medium in vivo.

In another embodiment, the present invention provides a method of forming a stable suspension of fused pyrrolocarbazole-containing, suspended particles, comprising:

(a) dissolving a fused pyrrolocarbazole in a non-aqueous liquid containing a surfactant in an amount from about 20% to greater than 99%, to form a particle-forming composition; and (b) contacting the particle-forming composition with an aqueous medium to form a stable suspension.

In another embodiment, the present invention provides a method of treating a disease or disorder in a mammal, comprising administering a therapeutically effective amount of a fused pyrrolocarbazole in a non-aqueous, particle-forming composition comprising a surfactant in an amount of at least 20% (w/w) to the mammal.

In another embodiment, the present invention provides a method of treating a disease or disorder in a mammal, comprising:

(a) contacting a fused pyrrolocarbazole in a non-aqueous, particle-forming composition comprising a surfactant in an amount of at least 20% (w/w) with an aqueous medium, thereby forming a stable suspension comprising suspended particles; and (b) administering a therapeutically effective amount of the stable suspension to the mammal.

In certain preferred embodiments the surfactant is present in at least 40% (w/w). In other preferred embodiments, the disease or disorder is a neurological disorder, or cancer such as prostate cancer. In other preferred embodiments, the subject is a mammal.

The materials, methods, and examples presented herein are intended to be illustrative, and not intended to limit the scope of the invention. All publications, patent applications, patents, and other references mentioned herein are incorporated by reference. Unless otherwise defined, all technical and scientific terms are intended to have their art-recognized meanings.

The present invention is directed to non-aqueous, particle-forming compositions which contain a fused pyrrolocarbazole, and a surfactant. Upon contact with an aqueous medium, the particle-forming composition spontaneously disperses into suspended particles, thereby forming a stable suspension that provides greatly improved bioavailability of orally administered fused pyrrolocarbazole compounds.

The particle-forming compositions of the present invention may be a liquid, semi-solid, or solid at room temperature. If liquid, the composition may be contained in a capsule. If semi-solid or solid, the composition can be in the form of a capsule or tablet.

As used herein, "non-aqueous" composition is intended to mean a composition that contains from 0% to about 10% water by weight. As used herein, "particle-forming composition" is intended to mean a composition that spontaneously disperses into suspended particles upon entry into an aqueous medium. As used herein, "suspended particle" is intended to mean a micelle, microsphere, droplet, or other substantially non-crystalline physical structure that remains suspended in an aqueous medium, without substantial phase separation. As used herein, "aqueous medium" is intended to mean any medium comprised of greater than 10% water, and in which the compositions of the present invention are particle-forming.

Initially, a fused pyrrolocarbazole is dissolved in a non-aqueous, particle-forming composition. Subsequently, the particle-forming composition is contacted with an aqueous medium to form an aqueous suspension. Upon contact with an aqueous medium, the fused pyrrolocarbazole-containing, non-aqueous, particle-forming composition spontaneously forms particles of a suitable size, i.e., without energy input. Thus, when initially dissolved in a non-aqueous, particle-forming composition, a fused pyrrolocarbazole may have a higher solubility as compared to its solubility when placed directly in a comparable aqueous suspension containing preformed particles.

The particle-forming composition can be contacted with an aqueous medium in vitro, i.e., subjected to predilution, prior to ingestion by a mammal. Alternatively, the initial contact with an aqueous medium can be in vivo, e.g., contact with aqueous contents of the gastrointestinal composition of a mammal.

When the particle-forming composition is subjected to predilution, the dilution ratio preferably is from about 1:1000 (1 part formulation to 999 parts aqueous medium) to about 1:2 (1 part formulation to 1 part aqueous medium). More preferably, the dilution ratio is from about 1:500 (1 part formulation to 499 parts aqueous medium) to about 1:3 (1 part formulation to 2 parts aqueous medium). By way of general guidance, for administration to humans a convenient ratio is about 1:250, which is a rough correspondence to a 1 ml unit dose dispersed in an 8-ounce glass of an aqueous liquid.

It has also been discovered that the resultant solution in which the fused pyrrolocarbazole-containing particles are suspended is a stable suspension. Preferably, the particles contained in this medium have a diameter less than 400 nm. More preferably, the particles have a diameter less than 100 nm.

The degree of optical transparency of a given volume of water containing a given amount of formulation gives a useful indication of particle size. This is because the particles scatter visible light, with the larger particles causing greater scattering. In general, the greater the optical transparency, the smaller the particle size. High optical transparency, i.e., bluish haze invisible or nearly invisible, generally indicates a particle size of less than 100 nm. A distinct bluish haze generally indicates a particle size from about 100 nm to about 400 nm. Without intending to be bound by theory, it is noted that particle size tends to be essentially constant for a given formulation, regardless of the dilution ratio. If particles fail to form, an increase in dilution ratio may be used to promote particle formation.

Whether a formulation according to the invention is a liquid, semi-solid, or solid at room temperature, may depend upon the selection of components, or other concerns such as commercial viability, administration and the like. For example, a semi-solid or solid formulation is convenient for manufacturing unit doses of a fused pyrrolocarbazole in the form of a capsule, including both hard gelatin and soft gelatin capsules, and tablets. When the liquid or solid formulation contacts an aqueous medium, e.g., gastrointestinal liquids, the formulation disperses into suspended particles in which the fused pyrrolocarbazole is biologically available.

Compositions whose inert components (i.e., components other than the fused pyrrolocarbazole) are all liquid at room temperature can be prepared by simply mixing the components without heating. The desired amount of fused pyrrolocarbazole can be weighed out and dissolved in the mixture of inert components, without heating. Moderate heating, preferably less than 60° C., can be applied to hasten complete mixing of the inert components, to hasten dissolution of the fused pyrrolocarbazole, or both.

Preparation of compositions containing one or more components that are solid at room temperature is carried out at a moderately elevated temperature, preferably less than 60° C. While moderate heating can be useful, excessive heating can cause decomposition of one or more components of the formulation. For example, decomposition of polysorbate 80 can occur at temperatures above 60° C. Instability of certain fused pyrrolocarbazoles has been observed in the presence of short chain polyethylene glycols, e.g., PEG 400, at temperatures in the range of about 60° C. to 90° C.

Decomposition of polysorbate 80 may occur if maintained at 90° C. for more than one hour. As will be appreciated by one those of ordinary skill in the art, any deleterious effects of heat accumulate with time. Therefore, when heat is applied, time and temperature will typically be balanced against one another.

There is wide latitude in formulation of all particle-forming compositions of the present invention. Preferably, all non-fused pyrrolocarbazole components in the particle-forming composition are food grade materials or GRAS (Generally Recognized As Safe) materials. Information on GRAS materials can be found in *Inactive Ingredient Guide*, published by the U.S. Food and Drug Administration (Division of Drug Information Resources, Rockville, Md.), the disclosure of which is hereby incorporated herein by reference in its entirety. *Inactive Ingredient Guide* provides a listing of all inactive ingredients present in approved or conditionally approved drug products currently marketed for human use.

The compositions of the present invention, preferably contain a surfactant. Although the surfactant may be present in any amount which results in a particle-forming composition, typical compositions contain from about 20% to greater than 99% of a surfactant. Preferably, the amount of surfactant is at least 30%, at least 40%, or at least 50%, depending upon the additional components of the composition.

Surfactants include, but are not limited to, polyoxyethylene stearates, polyoxyethylene castor oil, polyoxyethylene sorbitan fatty acid esters (sorbitans), polyethylene glycol ethers, saturated polyglycolized glycerides, fatty acid esters of polyethylene glycol, hydroxylated lecithins, medium chain monoglycerides, medium chain fatty acid esters, polyethylene/propylene glycol copolymers, polyethylene glycol stearate, d-α-tocopheryl polyethylene glycol succinate, polyoxyl stearate (e.g., Myrj® 52) and polyoxyl castor oil.

Polyoxyethylene sorbitan fatty acid esters (polysorbates) are non-ionic surfactants (detergents) that may consist of a mixture of fatty acids. Commercially available examples are Tween® 20 (polyoxyethylene (20) sorbitan monolaurate), Tween® 40 (polyoxyethylene (20) sorbitan monopalmitate), and Tween® 80 (polyoxyethylene (20) sorbitan monooleate).

A preferred polyethylene glycol ether is PEG-4-isooctylphenyl ether, a non-ionic surfactant. Commercially available examples of polyethylene glycol ether surfactants are Triton® X-100, Triton® X-114, Triton® X-405, and Triton® N-101. Non-ionic surfactants are preferred.

Examples of other useful surfactants are saturated polyglycolized glycerides consisting of mono-, di-, or triglycerides; di-fatty acid esters of polyethylene glycol, e.g., Gelucire® 44/14; hydroxylated lecithins, e.g., Centrolene® A; medium chain monoglycerides, e.g., glyceryl monocaprylate (Imwitor® 308, Capmul® MCM C-8); medium chain monoglycerides and diglycerides, e.g., glyceryl caprylate/caprate (Capmul® MCM); polyethylene/propylene glycol copolymers; block copolymers of ethylene oxide and propylene oxide (e.g., Poloxamer 188, Pluronic® F-68); ethoxylated castor oil (e.g., Cremophor® EL); and ethoxylated hydroxystearic acid (e.g., Solutol® HS 15). Some surfactants are solid or semisolid at room temperature, e.g., Poloxamer 188, glyceryl monocaprylate, and Gelucire® 44/14. Additional surfactants are those found in *The Handbook of Pharmaceutical Excipients*, 2nd Ed., published by The Pharmaceutical Press, London and American Pharmaceutical Association (1994), a common text in the field, which is hereby incorporated by reference in its entirety.

The particle-forming compositions may also include an organic solvent, a lipid, an antioxidant, or a combination of these components. Such components include those found in *The Handbook of Pharmaceutical Excipients*, and include any which are known in the art to be acceptable for use in pharmaceutical formulations. The selection of suitable components is within ordinary skill in the art.

In some embodiments of the invention, inclusion of an organic solvent improves solubility of the fused pyrrolocarbazoles in the particle-forming composition. Certain useful organic solvents form a solid (or semi-solid) at room temperature, e.g., polyethylene glycol 1450. The effectiveness of an organic solvent may depend, in part, on the particular fused pyrrolocarbazole included in the particle-forming composition. By way of general guidance, organic solvents include, but are not limited to, propylene carbonate, dimethyl isosorbide, benzyl alcohol, and glycols such as propylene glycol and polyethylene glycol (PEG). As used herein, "polyethylene glycol" or "PEG" means a liquid or solid polymer of the general formula $H(OCH_2CH_2)_nOH$, wherein n is at least 4.

In some embodiments of the invention, a suitable antioxidant is included as a component of the particle-forming composition. As used herein, "antioxidant" is intended to indicate any substance useful to retard deterioration by oxidation or to inhibit reactions promoted by oxygen or peroxides. Antioxidants include, but are not limited to, ascorbic acid; fatty acid esters of ascorbic acid, e.g., ascorbyl palmitate; butylated hydroxytoluene ("BHT"); propyl gallate; and butylated hydroxyanisole ("BHA"). An appropriate antioxidant also includes mixtures of antioxidants, such as a mixture of BHA, propyl gallate and citric acid. An antioxidant is particularly useful when the fused pyrrolocarbazole contains a functional group susceptible to oxidation, e.g., a thiol or a thioether. A specific example of such a fused pyrrolocarbazole is the indolocarbazole compound IIa-51, which contains two thioether functionalities. An antioxidant can function either by scavenging oxidative compounds or inhibiting oxidation reactions.

In some embodiments of the invention, a suitable lipid is included as a component of the particle-forming composition. As used herein, "lipid" is intended to indicate a fat, oil, wax, sterol, glycerol ether, triglyceride, or combination thereof. The inclusion of a lipid can change particle characteristics, including particle size. One way in which a lipid can change particle characteristics is by causing formation of a microemulsion rather than micelles. Lipid-induced changes in particle characteristics can also affect bioavailability.

Although the compositions described herein may conceivably employ any therapeutic substance with poor aqueous solubility characteristics, the particle-forming compositions preferably contain a fused pyrrolocarbazole. Preferably the fused pyrrolocarbazole is present in the particle-forming composition at a concentration of 1 to 300 mg/ml. More preferably, the fused pyrrolocarbazole is present at a concentration of 1 to 100 mg/ml. Even more preferably, the fused pyrrolocarbazole is present at a concentration of about 1 to 50 mg/ml.

As used herein, "fused pyrrolocarbazole" is intended to mean a compound having a fused pyrrolocarbazole core structure:

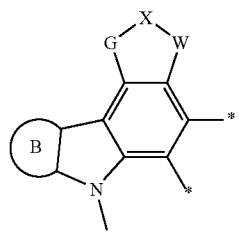

wherein at least one of G, X, or W is a nitrogen, B is an aryl or heteroaryl group, and * indicates the attachment point of an additional fused ring system.

The core structures provided herein are presented by way of general guidance, and are not to be taken as limiting the scope of the invention. For example, certain cores indicate the presence certain atoms for illustrative purposes. It will be appreciated that such atoms may bonded to additional groups, or may be further substituted without deviating from the spirit of the invention.

Thus, pyrrolocarbazole core structures include, but are not limited to, structures of formula Ia:

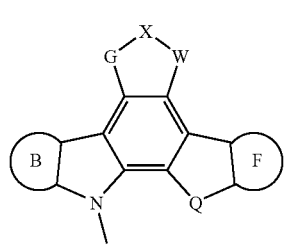

I-a wherein Q may be a moiety containing one or more nitrogens or carbons. Such structures include, but are not limited to, indolocarbazoles, indenocarbazoles, and bridged indenocarbazoles.

As used herein, "indolocarbazole" is intended to indicate a compound of formula Ia, wherein Q is nitrogen and Y is a bond:

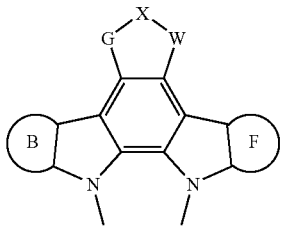

These compounds are intended to include, but are not limited to, structures in which the nitrogens of the carbazole and the indole form a cyclic bridged moiety:

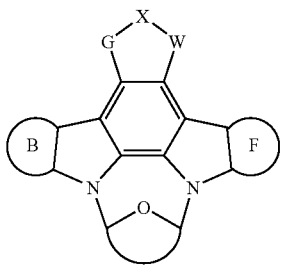

Such bridged structures include, but are not limited to, derivatives of the microbial-derived material referred to as K-252a.

As used herein, "indenocarbazole" is intended to indicate a compound of formula Ia in which Q is not nitrogen. These compounds include, but are not limited to, compounds wherein Q is one or more carbons. For example, in certain indenocarbazoles, Q is a single carbon:

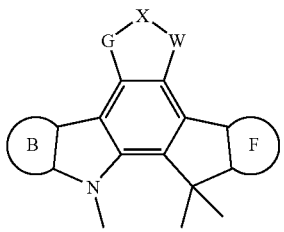

As used herein, "bridged indenopyrrolocarbazole" is intended to indicate a compound of formula Ia in which Q is a moiety containing at least one carbon which joins with the nitrogen of the carbazole derivative to form a bridged moiety:

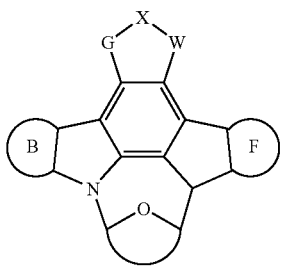

The fused pyrrolocarbazoles suitable for the particle-forming compositions of the present invention are stable compounds. As used herein "stable compound" or "stable structure" is meant to indicate a compound that is sufficiently robust to survive isolation to a useful degree of purity from a reaction mixture, and preferably capable of formulation into an efficacious therapeutic agent.

The fused pyrrolocarbazoles may be further substituted. As used herein, "substituted" is intended to indicate that one or more hydrogen atoms on the indicated atom is replaced with a selected group referred to herein as a "substituent", provided that the substituted atom's valency is not exceeded, and that the substitution results in a stable compound.

As used herein, the term "alkyl" means a straight-chain, cyclic, or branched alkyl group having 1 to 8 carbon atoms, such as methyl, ethyl, propyl, isopropyl, butyl, isobutyl, sec-butyl, tert-butyl, pentyl, isoamyl, neopentyl, 1-ethylpropyl, hexyl, octyl, cyclopropyl, and cyclopentyl. The alkyl moiety of alkyl-containing groups, such as alkoxy, alkoxycarbonyl, and alkylaminocarbonyl groups, has the same meaning as alkyl defined above. Lower alkyl groups, which are preferred, are alkyl groups as defined above which contain 1 to 4 carbons.

Alkyl groups and alkyl moieties contained within substituent groups such as aralkyl, alkoxy, arylalkoxy, hydroxyalkoxy, alkoxy-alkoxy, hydroxy-alkylthio, alkoxy-alkylthio, alkylcarbonyloxy, hydroxyalkyl and acyloxy groups may be substituted or unsubstituted. A substituted alkyl group has 1 to 3 independently-selected substituents, preferably hydroxy, lower alkoxy, lower alkoxy-alkoxy, substituted or unsubstituted arylalkoxy-lower alkoxy, substituted or unsubstituted heteroarylalkoxy-lower alkoxy, substituted or unsubstituted arylalkoxy, substituted or unsubstituted heterocycloalkoxy, halogen, carboxyl, lower alkoxycarbonyl, nitro, amino, mono- or di-lower alkylamino, dioxolane, dioxane, dithiolane, dithione, furan, lactone, or lactam.

As used herein, the term "alkenyl" is intended to include straight-chain, cyclic, or branched hydrocarbon chains having at least one carbon-carbon double bond. Examples of alkenyl groups include ethenyl, propenyl, 3-methylbutenyl, and cyclohexenyl groups. As used herein, the term "alkynyl" is intended to include straight-chain, cyclic, or branched hydrocarbon chains having at least one carbon-carbon triple bond. Examples of alkynyl groups include ethynyl, propynyl, 3-methylbutynyl, and cyclohexynyl groups.

As used herein, the "acyl" moiety of acyl-containing groups such as acyloxy groups is intended to include a straight-chain, branched, or cyclic alkanoyl group having 1 to 6 carbon atoms, such as formyl, acetyl, propanoyl, butyryl, valeryl, pivaloyl or hexanoyl.

As used herein, the term "carbocyclic" refers to cyclic groups in which the ring portion is composed solely of carbon atoms. These include, but are not limited to, cyclopropyl, cyclobutyl, cyclopentyl, cyclohexyl, cycloheptyl, cyclooctyl. The term "carbocyclic aromatic ring" is intended to include carbocyclic rings which are also aryl rings. The terms "heterocyclo" and "heterocyclic" refer to cyclic groups in which the ring portion includes at least one heteroatom such as O, N, or S. Heterocyclyl groups include heteroaryl and heteroalkyl groups.

As used herein the term "aryl" means an aromatic ring having 6 to 12 carbon atoms such as phenyl, biphenyl and naphthyl. Preferred aryl groups include unsubstituted or substituted phenyl and naphthyl groups. The term "heteroaryl" as used herein denotes an aryl group in which one or more ring carbon atoms is replaced by a hetero (i.e., non-carbon) atom such as O, N or S. Preferred heteroaryl groups include pyridyl, pyrimidyl, pyrrolyl, furyl, thienyl, imidazolyl, triazolyl, tetrazolyl, quinolyl, isoquinolyl, benzoimidazolyl, thiazolyl, pyrazolyl, and benzothiazolyl groups. The term "heteroalkyl" denotes a cycloalkyl group in which one or more ring carbon atoms is replaced by hetero atoms such as O, N, or S.

As used herein, the term "aralkyl" (or "arylalkyl") is intended to denote a group having from 7 to 15 carbons, consisting of an alkyl group that bears an aryl group. Examples of aralkyl groups include, but are not limited to, benzyl, phenethyl, benzhydryl and naphthylmethyl groups. Substituted aryl, substituted heterocyclic and substituted aralkyl groups each have 1 to 3 independently selected substituents that are preferably lower alkyl, hydroxy, lower alkoxy, carboxy, lower alkoxycarbonyl, nitro, amino, mono- or di-lower alkylamino, and halogen.

Preferred heterocyclic groups formed with a nitrogen atom include pyrrolidinyl, piperidinyl, piperidino, morpholinyl, morpholino, thiomorpholino, N-methylpiperazinyl, indolyl, isoindolyl, imidazole, imidazoline, oxazoline, oxazole, triazole, thiazoline, thiazole, isothiazole, thiadiazoles, triazines, isoxazole, oxindole, indoxyl, pyrazole, pyrazolone, pyrimidine, pyrazine, quinoline, isoquinoline, and tetrazole groups. Preferred heterocyclic groups formed with an oxygen atom include furan, tetrahydrofuran, pyran, benzofurans, isobenzofurans, and tetrahydropyran groups. Preferred heterocyclic groups formed with a sulfur atom include thiophene, thianaphthene, tetrahydrothiophene, tetrahydrothiapyran, and benzothiophenes.

As used herein, "hydroxyalkyl" groups are alkyl groups that have a hydroxyl group appended thereto. As used herein, "hydroxyalkoxy" groups are alkoxy groups that have a hydroxyl group appended thereto. As used herein, "halogen" refers to fluorine, chlorine, bromine and iodine.

As used herein, the term "heteroarylalkyl" means an arylalkyl group that contains a heteroatom in the aryl moiety. The term "oxy" denotes the presence of an oxygen atom. Thus, "alkoxy" groups are alkyl groups that are attached through an oxygen atom, and "carbonyloxy" groups are carbonyl groups that are attached through an oxygen atom.

As used herein, the terms "heterocycloalkyl" and "heterocycloalkoxy" mean an alkyl or an alkoxy group that has a heterocyclo group attached to the alkyl moiety thereof, and the term "arylalkoxy" means an alkoxy group that has an aryl group attached to the alkyl moiety thereof. As used herein, the term "alkylcarbonyloxy" means a group of formula —O—C(=O)-alkyl.

As used herein, the term "alkyloxy-alkoxy" denotes an alkoxy group that contains an alkyloxy substituent attached to its alkyl moiety. The term "alkoxy-alkylthio" means an alkylthio group (i.e., a group of formula —S-alkyl) that contains an alkoxy substituent attached to its alkyl moiety. The term "hydroxy-alkylthio" means an alkylthio group (i.e., a group of formula —S-alkyl) that contains a hydroxy substituent attached to its alkyl moiety.

As used herein, the term "monosaccharide" has its accustomed meaning as a simple sugar. As used herein, the term "amino acid" denotes a molecule containing both an amino group and a carboxyl group. Embodiments of amino acids include a-amino acids; i.e., carboxylic acids of general formula HOOC—CH(NH2)-(side chain). Side chains of amino acids include naturally occurring and non-naturally occurring moieties. Non-naturally occurring (i.e., unnatural) amino acid side chains are moieties that are used in place of naturally occurring amino acid side chains in, for example, amino acid analogs. See, for example, Lehninger, *Biochemistry*, Second Edition, Worth Publishers, Inc, 1975, pages 73-75, incorporated by reference herein. In certain embodiments, substituent groups for the compounds described herein include the residue of an amino acid after removal of the hydroxyl moiety of the carboxyl group thereof; i.e., groups of Formula —C(=O)CH(NH$_2$)-(side chain).

The fused pyrrolocarbazoles are preferably present in the compositions described herein in a therapeutically effective amount. As used herein, a "therapeutically effective amount" refers to an amount of compound effective to prevent or treat the symptoms of particular disorder. Such disorders include, but are not limited to, those pathological and neurological disorders associated with the aberrant activity of target receptors, wherein the treatment or prevention comprises inhibiting, inducing, or enhancing the activity thereof by contacting the receptor with an active drug substance. As will be readily understood, the concentration and dosages of the fused pyrrolocarbazoles will depend upon factors such as the total dosage of the drug to be administered, the chemical characteristics of the compounds employed, the route of administration, the age, body weight and symptoms of the patient, etc. By way of general guidance, human doses may range from about 0.1 mg to about 1000 mg administered per day. Preferably, the dosage is about 1 to about 500 mg administered two times a day. Even more preferably, the dosage is about 10 mg to about 300 mg, two times per day.

The fused pyrrolocarbazole may be present in various forms as will be appreciated by the skilled artisan. Such forms include, but are not limited to, pharmaceutically acceptable salts, prodrugs, polymorphs, stereoisomers, and the like. As used herein, the term "pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two. Generally, non-aqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., 1985, p. 1418, the disclosure of which is hereby incorporated by reference.

The fused pyrrolocarbazoles of the present invention may exist in prodrug form. As used herein, "prodrug" is intended to include any covalently bonded carriers which release the active parent drug according to Formula I or other formulas or compounds of the present invention in vivo when such prodrug is administered to a mammalian subject. Since prodrugs are known to enhance numerous desirable qualities of pharmaceuticals (e.g., solubility, bioavailability, manufacturing, etc.) the compounds of the present invention may be delivered in prodrug form. Thus, the present invention contemplates prodrugs of the claimed compounds, compositions containing the same, and methods of delivering the same. Prodrugs of a compound of the present invention, for example Formula I, may be prepared by modifying functional groups present in the compound in such a way that the modifications are cleaved, either in routine manipulation or in vivo, to the parent compound.

Accordingly, prodrugs include, for example, compounds of the present invention wherein a hydroxy, amino, or carboxy group is bonded to any group that, when the prodrug is administered to a mammalian subject, cleaves to form a free hydroxyl, free amino, or carboxylic acid, respectively. Examples include, but are not limited to, acetate, formate and benzoate derivatives of alcohol and amine functional groups; and alkyl, carbocyclic, aryl, and alkylaryl esters such as methyl, ethyl, propyl, iso-propyl, butyl, isobutyl, sec-butyl, tert-butyl, cyclopropyl, phenyl, benzyl, and phenethyl esters, and the like.

The compounds of the present invention may be prepared in a number of ways well known to those skilled in the art. The compounds can be synthesized, for example, by the methods described below, or variations thereon as appreciated by the skilled artisan. All processes disclosed in association with the present invention are contemplated to be practiced on any scale, including milligram, gram, multigram, kilogram, multikilogram or commercial industrial scale.

It will be appreciated that the compounds of the present invention may contain one or more asymmetrically substituted carbon atoms, and may be isolated in optically active or racemic forms. Thus, all chiral, diastereomeric, racemic forms and all geometric isomeric forms of a structure are intended, unless the specific stereochemistry or isomeric form is specifically indicated. It is well known in the art how to prepare and isolate such optically active forms. For example, mixtures of stereoisomers may be separated by standard techniques including, but not limited to, resolution of racemic forms, normal, reverse-phase, and chiral chromatography, preferential salt formation, recrystallization, and the like, or by chiral synthesis either from chiral starting materials or by deliberate synthesis of target chiral centers.

As will be readily understood, functional groups present may contain protecting groups during the course of synthesis. For example, the amino acid side chain substituents of the compounds of Formula Ia can be substituted with protecting groups such as benzyloxycarbonyl or t-butoxycarbonyl groups. Protecting groups are known per se as chemical functional groups that can be selectively appended to and removed from functionalities, such as hydroxyl groups and carboxyl groups. These groups are present in a chemical compound to render such functionality inert to chemical reaction conditions to which the compound is exposed. Any of a variety of protecting groups may be employed with the present invention. Preferred protecting groups include the benzyloxycarbonyl (Cbz; Z) group and the tert-butyloxycarbonyl (Boc) group. Other preferred protecting groups according to the invention may be found in Greene, T. W. and Wuts, P. G. M., *Protective Groups in Organic Synthesis* 2d. Ed., Wiley & Sons, 1991.

Fused pyrrolocarbazoles, such as indolocarbazoles may be synthesized by methods taught, for example, in U.S. Pat. Nos. 4,923,986; 4,877,776; 5,093,330; 5,461,146; 5,468,872; 5,621,100; 5,621,101; 5,516,771; and 5,599,808; and PCT publication Nos. WO 93/08809 and WO 97/46565, the disclosures of which are hereby incorporated herein by reference in their entirety. Additional methods of preparation are set forth in Moody et al., *J. Org. Chem.* 57:2105-2114 (1992), also incorporated herein by reference.

Fused pyrrolocarbazoles, such as indenocarbazoles, as well as additional compounds wherein Q is not a single nitrogen, may be synthesized by methods taught, for example, in U.S. Pat. Nos. 5,475,110; 5,591,855; 5,594,009; 5,705,511; 5,616,724; and 5,801,190; the disclosures of which are hereby incorporated herein by reference in their entirety.

Fused pyrrolocarbazoles, such as bridged indenocarbazoles, may be prepared by methods taught, for example, in U.S. patent application Ser. No. 09/325,140, the disclosure of which is hereby incorporated herein by reference in its entirety.

The fused pyrrolocarbazoles disclosed in all foregoing references are contemplated for use in the particle-forming compositions of the present invention. Other exemplary fused pyrrolocarbazoles are the indolocarbazoles set forth in Tables I-A and I-B, wherein each entry corresponds to the accompanying structure.

TABLE I-A

II-a

| Compound | R⁴ | R³ | R¹⁵ | R¹⁶ | Z¹; Z² |
|---|---|---|---|---|---|
| IIa-1 | H | H | CH₂N₃ | OH | H; H |
| IIa-2 | NHCONHC₆H₅ | H | CO₂CH₃ | OH | H; H |
| IIa-3 | CH₂SOC₂H₅ | H | CO₂CH₃ | OH | H; H |
| IIa-4 | H | H | CH₂OH | OCH₃ | H; H |
| IIa-5 | H | H | CONHC₂H₅ | OH | H; H |
| IIa-6 | H | H | CH=NNH-2-imidazoline | OH | H; H |
| IIa-7 | H | H | CH₂NH-Gly | OH | H; H |
| IIa-8 | H | H | CON(CH₃)₂ | OH | H; H |
| IIa-9 | H | H | —CH₂NHCO₂— | (with X) | H; H |
| IIa-10 | Br | H | CO₂CH₃ | OH | H; H |
| IIa-11 | H | H | CONH₂ | OH | H; H |
| IIa-12 | H | H | CH₂OH | OH | H; H |
| IIa-13 | H | H | CONHC₃H₇ | OH | H; H |
| IIa-14 | H | H | CH₂NH-Serine | OH | H; H |
| IIa-15 | H | H | CH₂SOCH₃ | OH | H; H |
| IIa-16 | H | H | CH=NOH | OH | H; H |
| IIa-17 | H | H | CON-morpholine | OH | H; H |
| IIa-18 | H | H | CH₂NH-Proline | OH | H; H |
| IIa-19 | H | H | CH=NNHC(=NH)NH₂ | OH | H; H |
| IIa-20 | Br | Br | CO₂CH₃ | OH | =O |
| IIa-21 | H | H | CONH(CH₂)₂OH | OH | H; H |
| IIa-22 | H | H | CO₂CH₃ | OH | =O |
| IIa-23 | H | H | H | OH | H; H |
| IIa-24 | H | H | CH=NNHCONH₂ | OH | H; H |
| IIa-25 | H | H | CH₂OCOCH₃ | OH | H; H |
| IIa-26 | H | H | —CH₂OC(CH₃)₂O— | (with X) | H; H |
| IIa-29 | NHCONHC₂H₅ | H | CO₂CH₃ | OH | H; H |
| IIa-30 | CH₂SC₂H₅ | H | CO₂CH₃ | OH | H; H |
| IIa-31 | Br | H | CH₂OH | OH | H; H |
| IIa-32 | Br | Br | CO₂CH₃ | OH | H; H |
| IIa-33 | CH₂SC₆H₅ | H | CO₂CH₃ | OH | H; H |
| IIa-34 | Cl | Cl | CO₂CH₃ | OH | H; H |
| IIa-36 | H | H | CONHC₆H₅ | OH | H; H |
| IIa-37 | H | H | CH₂SO | OH | H; H |
| IIa-38 | H | H | CH₂NHCO₂C₆H₅ | OH | H; H |
| IIa-39 | NHCONHC₂H₅ | NHCONHC₂H₅ | CO₂CH₃ | OH | H; H |
| IIa-40 | N(CH₃)₂ | H | CO₂CH₃ | OH | H; H |
| IIa-41 | CH₃ | H | CO₂CH₃ | OH | H; H |
| IIa-42 | CH₂OCONHC₂H₅ | H | CO₂CH₃ | OH | H; H |
| IIa-43 | NHCO₂CH₃ | H | CO₂CH₃ | OH | H; H |
| IIa-44 | Br | Br | CH₂OH | OH | H; H |
| IIa-45 | Br | Br | CONHC₆H₅ | OH | H; H |
| IIa-46 | Br | Br | CONHCH₂CH₂OH | OH | H; H |
| IIa-47 | CH₂OC₂H₅ | H | CO₂CH₃ | OH | H; H |
| IIa-48 | CH₂N(CH₃)₂ | H | CO₂CH₃ | OH | H; H |
| IIa-49 | CH₂SO₂C₂H₅ | H | CO₂CH₃ | OH | H; H |
| IIa-50 | CH₂S | H | CO₂CH₃ | OH | H; H |
| IIa-51 | CH₂SC₂H₅ | CH₂SC₂H₅ | CO₂CH₃ | OH | H; H |
| IIa-52 | CH=NNH | H | CO₂CH₃ | OH | H; H |
| IIa-53 | CH₂S | H | CO₂CH₃ | OH | H; H |
| IIa-54 | CH₂S(O) | H | CO₂CH₃ | OH | H; H |
| IIa-55 | CH₂S(O) | H | CO₂CH₃ | OH | H; H |
| IIa-56 | CH₂SC₂H₅ | CH₂OH | CO₂CH₃ | OH | H; H |
| IIa-57 | H | H | CH₂NHCO₂CH₃ | OH | H; H |
| IIa-58 | Br | H | CONH₂ | OH | H; H |
| IIa-59 | H | H | CH₂SC₆H₅ | OH | H; H |
| IIa-60 | H | H | CH₂S-2-pyridyl | OH | H; H |
| IIa-61 | H | H | CH₂SOC₆H₅ | OH | H; H |

TABLE I-B

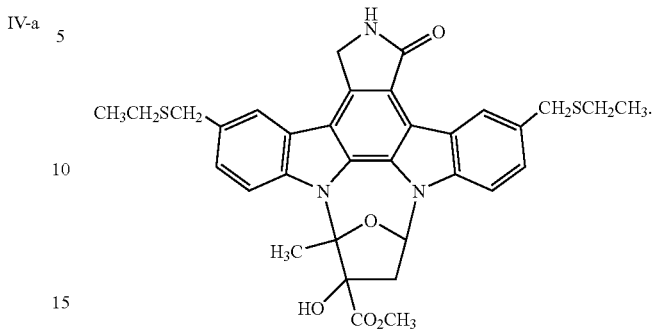

IV-a

| Compound | R⁴ | R³ | R² | R⁶ | Z¹; Z² |
|---|---|---|---|---|---|
| IVa-1[1] | H | H | CH$_2$CH=CH$_2$ | H | H; H |
| IVa-2 | Br | H | H | H | H; H |
| IVa-3 | H | H | CH$_2$CH=CH$_2$ | CH$_2$CH=CH$_2$ | H; H |
| IVa-4[1] | H | H | H | CH$_2$CH=CH$_2$ | H; H |
| IVa-5 | H | H | H | H | =O |
| IVa-6 | H | H | H | H | H; H |

[1]IVa-1 and IVa-4 are a 1.5 to 1.0 mixture of the components.

Certain preferred indolocarbazoles are compounds designated by formula IIa-4, IIa-12, and IIa-51 having the following structures.

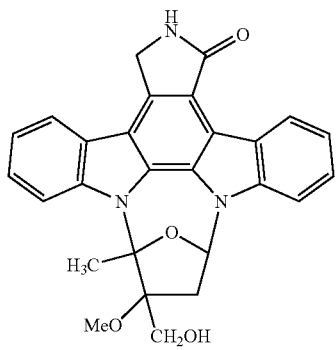

IIa-4

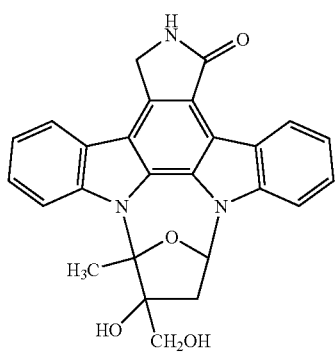

IIa-12

IIa-51

The non-aqueous particle-forming compositions of the invention provide greatly improved bioavailability of fused pyrrolocarbazoles. For example, in water Compound IIa-12 has essentially no solubility. In pure Tween 80, it has a solubility of 28.43 mg/ml. When placed directly in an aqueous solution of 2% Tween 80, Compound IIa-12 has a solubility of 0.18 mg/ml. When initially dissolved in Tween 80 (a particle-forming composition) and subsequently diluted 50-fold with water (to produce an aqueous solution of 2% Tween 80), the final solubility is 0.57 mg/ml.

Thus, dissolving the fused pyrrolocarbazole initially in this particular particle-forming composition achieves a better than 3.2-fold increase in fused pyrrolocarbazole concentration in the final solution. Because initial contact with an aqueous medium occurs in vitro or in vivo, the non-aqueous particle-forming compositions are useful for therapeutic administration of a fused pyrrolocarbazole to a mammal.

The present invention also features a method of forming a stable suspension of fused pyrrolocarbazole-containing particles. The method typically includes: (a) dissolving an fused pyrrolocarbazole in a non-aqueous liquid containing a surfactant in an amount from about 20% to greater than 99%, thereby forming an fused pyrrolocarbazole-containing, particle-forming composition, and (b) contacting the particle-forming composition with an aqueous medium. The particle-forming composition can be contacted with the aqueous medium in vitro or in vivo. Preferably, the amount of surfactant is at least 30%, and more preferably, it is at least 40%, with 50% being particularly preferred. The particle-forming composition optionally includes an organic solvent, a lipid, an antioxidant, or a combination of those components.

The present invention additionally features methods for preparing the particle-forming compositions described herein. In one embodiment, the first step involves heating at least one organic solvent. Preferably the solvent is heated at a temperature that either liquefies those solvents that are solid or semi-solid at room temperature, or that maximizes the solubilization of the active agent, but below that which leads to degradation or instability of the mixture. Some compositions may require addition of at least one antioxidant to minimize degradation of the composition. The second step involves mixing the active agent into the heated solvent or heated solvent mixture. The active agent includes the fused pyrrolocarbazoles disclosed herein. Preferably the mixing is done at a high speed, with a high shear mixing device or homogenizer to minimize the amount of mixing time and to thoroughly disperse the active agent. Preferably the resultant mixture is homogenized mixture. The third step involves addition of the surfactant and any additional excipients to the homogenized mixture. Preferably the additional excipients are stirred into the homogenized mixture, or mixed in at a low speed. The resultant composition can be dispensed into gelatin or HPMC capsules as a warm solution and allowed to solidify. Alternatively, the solution can be slab cooled or spray congealed and further processed by milling, granulating and blending and dry-powder filled into gelatin or HPMC capsules.

In a further embodiment, the method for preparation of the compositions of the present invention comprises heating at least one organic solvent and optionally one or more antioxidants, followed by addition of a fused pyrrolocarbazole and mixing with a high shear homogenizer, followed by addition of one or more surfactants. In particular, the present invention includes a method for preparing a composition of comprising a fused pyrrolocarbazole, at least one organic solvent, at least one surfactant, and optionally at least one antioxidant wherein the compassion is non-aqueous and particle-forming comprising:

(a) heating the organic solvent and optionally the antioxidant to about 50-90° C. to form a heated mixture;

(b) mixing the fused pyrrolocarbazole in the heated mixture with a high shear homogenizer to form a homogenized mixture; and (c) mixing the surfactant to the homogenized mixture.

Preferably, at least one antioxidant is heated with the organic solvent. Preferably the temperature range is 50-70° C., and more preferably is 60-70° C.

The invention also features a method of treating a neurological disease or disorder in a mammal, e.g., a human. The method includes formulating a fused pyrrolocarbazole in a non-aqueous, fused pyrrolocarbazole-containing, particle-forming composition containing a surfactant in an amount of at least 20% (w/w), and administering a therapeutically effective amount of the particle-forming composition to the mammal. In one embodiment of the method, the particle-forming composition is contacted with an aqueous medium in vitro, to form a stable suspension. A therapeutically effective amount of he stable suspension is then administered to the mammal. In an alternative embodiment, a therapeutically effective amount of the particle-forming composition is administered directly to the mammal, where it contacts an aqueous medium in vivo.

The invention also features a method of treating cancer, including prostate cancer and acute myelogenous leukemia, in a mammal, e.g., a human. The method of treating acute myelogenus leukemia includes formulating a fused pyrrolocarbazole in a non-aqueous, fused pyrrolocarbazole-containing, particle-forming composition containing a surfactant in an amount of at least 20% (w/w), and administering a therapeutically effective amount of the particle-forming composition to the mammal. In one embodiment of the method, the particle-forming composition is contacted with an aqueous medium in vitro, to form a stable suspension. A therapeutically effective amount of the stable suspension is then administered to the mammal. In an alternative embodiment, a therapeutically effective amount of the particle-forming composition is administered directly to the mammal, where it contacts an aqueous medium in vivo.

The invention is further illustrated by the following examples. The examples are provided for illustration purposes only, and they are not to be construed as limiting the scope or content of the invention.

EXAMPLES

Formulations

Numerous particle-forming compositions according to the invention have been formulated using various components in various amounts relative to one another. The formulations for several particle-forming compositions are presented in Table 2, below.

TABLE 2

Exemplary Formulations

| Form No. | Component (category) | Component (specific) | Amount | Solid/Liq (room temp) |
|---|---|---|---|---|
| 1 | indolocarbazole | Compound IIa-51 | 100 mg/ml | solid |
|  | organic solvent | PEG 1450 | 70% |  |
|  | surfactant | Poloxamer 188 | 30% |  |
| 2 | indolocarbazole | Compound IIa-51 | 100 mg/ml | liquid |
|  | organic solvent | PEG 400 | 70% |  |
|  | surfactant | polysorbate 80 | 30% |  |
| 3 | indolocarbazole | Compound IIa-51 | 100 mg/ml | solid |
|  | organic solvent | PEG 1450 | 60% |  |
|  | organic solvent | propylene glycol | 20% |  |
|  | surfactant | Poloxamer 188 | 20% |  |
| 4 | indolocarbazole | Compound IIa-51 | 25 mg/ml | liquid |
|  | organic solvent | PEG 400 | 25% |  |
|  | organic solvent | propylene glycol | 25% |  |
|  | surfactant | polysorbate 80 | 50% |  |
| 5 | indolocarbazole | Compound IIa-51 | 5 mg/ml | liquid |
|  | organic solvent | PEG 400 | 25% |  |
|  | organic solvent | propylene carbonate | 25% |  |
|  | surfactant | polysorbate 80 | 50% |  |
| 6 | indolocarbazole | Compound IIa-51 | 5 mg/ml | liquid |
|  | organic solvent | Propylene glycol | 47.5% |  |
|  | surfactant | glyceryl monocaprylate | 47.5% |  |
|  | surfactant | Poloxamer 188 | 5% |  |
| 7 | indolocarbazole | Compound IIa-51 | 25 mg/ml | liquid |
|  | organic solvent | propylene glycol | 25% |  |
|  | surfactant | glyceryl monocaprylate | 25% |  |
|  | surfactant | polysorbate 80 | 50% |  |
| 8 | indolocarbazole | Compound IIa-51 | 1 mg/ml | liquid |
|  | organic solvent | propylene glycol | 40% |  |
|  | surfactant | glyceryl monocaprylate | 30% |  |
|  | surfactant | glyceryl caprylate-caprate | 30% |  |
| 9 | indolocarbazole | Compound IIa-51 | 50 mg/ml | liquid |
|  | organic solvent | propylene glycol | 50% |  |
|  | organic solvent | propylene carbonate | 25% |  |
|  | surfactant | polysorbate 80 | 25% |  |
| 10 | indolocarbazole | Compound IIa-51 | 100 mg/ml | solid |
|  | surfactant | glyceryl monocaprylate | 100% |  |
| 11 | indolocarbazole | Compound IIa-51 | 100 mg/ml | solid |
|  | surfactant | glyceryl monocaprylate | 70% |  |
|  | surfactant | Poloxamer 188 | 30% |  |
| 12 | indolocarbazole | Compound IIa-12 | 25 mg/ml | solid |
|  | organic solvent | propylene glycol | 40% |  |
|  | surfactant | Gelucire® 44/14 | 60% |  |
| 13 | indolocarbazole | Compound IIa-12 | 25 mg/ml | liquid |
|  | organic solvent | propylene glycol | 30% |  |
|  | lipid | Captex® 200 | 14% |  |
|  | surfactant | Capmul® MCM C-8 | 11% |  |
|  | surfactant | polysorbate 80 | 45% |  |
| 14 | indolocarbazole | Compound IIa-12 | 25 mg/ml | liquid |
|  | organic solvent | propylene glycol | 30% |  |
|  | lipid | Captex® 200 | 14% |  |
|  | surfactant | Centrolene® A | 11% |  |
|  | surfactant | polysorbate 80 | 45% |  |

TABLE 2-continued

Exemplary Formulations

| Form No. | Component (category) | Component (specific) | Amount | Solid/Liq (room temp) |
|---|---|---|---|---|
| 15 | indolocarbazole | Compound IIa-12 | 25 mg/ml | liquid |
|  | organic solvent | propylene glycol | 30% |  |
|  | lipid | Captex® 200 | 14% |  |
|  | surfactant | Imwitor® 308 | 11% |  |
|  | surfactant | polysorbate 80 | 45% |  |
| 16 | indolocarbazole | Compound IIa-12 | 25 mg/ml | liquid |
|  | organic solvent | propylene glycol | 50% |  |
|  | surfactant | polysorbate 80 | 50% |  |
| 17 | indolocarbazole | Compound IIa-12 | 16.7 mg/ml | solid |
|  | organic solvent | propylene glycol | 10% |  |
|  | surfactant | Gelucire7 44/14 | 90% |  |
| 18 | indolocarbazole | Compound IIa-12 | 25 mg/ml | liquid |
|  | organic solvent | propylene glycol | 10% |  |
|  | organic solvent | propylene carbonate | 40% |  |
|  | surfactant | polysorbate 80 | 50% |  |
| 19 | indolocarbazole | Compound IIa-12 | 25 mg/ml | liquid |
|  | organic solvent | propylene glycol | 10% |  |
|  | organic solvent | dimethyl-isosorbide | 40% |  |
|  | surfactant | polysorbate 80 | 50% |  |
| 20 | indolocarbazole | Compound IIa-12 | 15 mg/ml | solid |
|  | surfactant | Gelucire® 44/14 | 100% |  |
| 21 | indolocarbazole | Compound IIa-51 | 1 mg/ml | solid |
|  | organic solvent | propylene glycol | 25% |  |
|  | surfactant | Gelucire® 44/14 | 75% |  |
| 22 | indolocarbazole | Compound IIa-51 | 100 mg/ml | solid |
|  | surfactant | Gelucire® 44/14 | 100% |  |
| 23 | indolocarbazole | Compound IIa-51 | 12 mg/ml | liquid |
|  | surfactant | Poloxamer 184 | 90% |  |
|  | surfactant | Capmul® MCM | 10% |  |

Other exemplary formulations include compositions comprising a fused pyrrolocarbazole, a polyethylene glycol and a polyoxyl stearate. In certain embodiments, the fused pyrrolocarbazole is compound IIa-4, IIa-12, or IIa-51. In other embodiments, the polyethylene glycol has a molecular weight from about 300 to 8000 Daltons, or preferably from 400-3350 Daltons, or more preferably from 400-1500 Daltons. In other embodiments, the polyoxyl stearate is Myrj® 52.

In additional exemplary formulations, the fused pyrrolocarbazole is compound IIa-12, and the polyethylene glycol is PEG-400, PEG-600, PEG-1000, or PEG-1450 and the surfactant is polyoxyl stearate is Myrj® 52. The ratio of polyethylene glycol:polyoxyl stearate ranges from 50:50 to 80:20, preferably the ratio is 50:50 or 80:20.

In other exemplary formulations, the organic solvent can be a mixture of polyethylene glycols. In one embodiment, the polyethylene glycols are selected from PEG-400, PEG-600, PEG-1000 and PEG-1450. In other embodiments, the mixture of polyethylene glycols can be PEG-400/PEG-1000, PEG-400/PEG-1450, PEG-600/PEG-1000, PEG-600/PEG-1450. In further embodiments, the surfactant is a polyoxyl stearate, and is preferably Myrj® 52. The ratio of a polyethylene glycol mixture:polyoxyl stearate ranges from 50:50 to 80:20, preferably the ratio is 50:50 or 80:20. In certain embodiments the composition comprises PEG-400:PEG-1000:polyoxyl stearate in a ratio of 25:25:50, or PEG-400:PEG-1450:polyoxyl stearate in a ratio of 25:25:50, or PEG-600:PEG-1000:polyoxyl stearate in a ratio of 25:25:50, or PEG-600:PEG-1450:polyoxyl stearate in a ratio of 25:25:50. In other embodiments, the composition comprises PEG-400:PEG-1000:polyoxyl stearate in a ratio of 40:40:20, or PEG-400:PEG-1450:polyoxyl stearate in a ratio of 40:40:20, or PEG-600:PEG-1000:polyoxyl stearate in a ratio of 40:40:20, or PEG-600:PEG-1450:polyoxyl stearate in a ratio of 40:40:20.

Bioavailability in Rats

Compound IIa-12 has displayed anticancer activity in a rat tumor model of prostate cancer. A bioavailability study involving Compound IIa-12 formulated in non-aqueous, particle forming compositions was carried out using rats. Pharmacokinetic parameters were measured following intravenous (i.v.) administration and oral (p.o.) administration to the rats. In addition, the absolute oral bioavailability (F) of Compound IIa-12 was examined after single administration of three different formulations.

Male Sprague-Dawley rats were given either a bolus i.v. dose administered into the tail vein, or p.o. doses by gavage in one of three formulations. The formulations were as described in Table 2A, below. Formulation (a) is not a particle-forming composition.

TABLE 2A

Formulations in Rat Study

| Form. | Component (category) | Component (specific) | Amount | Solid/Liq. (room temp.) |
|---|---|---|---|---|
| (a) | indolocarbazole | Compound IIa-12 | 5 mg/ml | liquid |
|  | organic solvent | PEG 1000 | 40% |  |
|  | organic solvent | PVP C30 | 10% |  |
|  | organic solvent | benzyl alcohol | 2% |  |
|  | water | water | 48% |  |
| (b) | indolocarbazole | Compound IIa-12 | 5 mg/ml | solid |
|  | organic solvent | propylene glycol | 25% |  |
|  | surfactant | Gelucire® 44/14 | 75% |  |
| (c) | indolocarbazole | Compound IIa-12 | 5 mg/ml | liquid |
|  | organic solvent | propylene glycol | 30% |  |
|  | surfactant | Capmul® MCM C-8 | 11% |  |
|  | surfactant | Captex® | 14% |  |
|  | surfactant | Polysorbate 80 | 45% |  |

Blood samples were collected at predetermined time points. Plasma levels of Compound IIa-12 were determined by HPLC. The mean values for the pharmacokinetic parameters are summarized in Table 3, below. In Table 3, $C_{max}$ is peak plasma concentration; $T_{max}$ is time to peak plasma concentration; $T_{t/2}$ is apparent elimination half-life; $AUC_{0-4}$ is area under the curve (serum conc. vs. time); and F % is absolute bioavailability (total dose/AUC).

TABLE 3

Pharmacokinetic Data Summary

| Route/Form | Dose mg/kg | $C_{max}$ ng/mL | $T_{max}$ hr | $T_{t/2}$ hr | $AUC_{0-4}$ ng·hr/mL | F % |
|---|---|---|---|---|---|---|
| i.v. (a) | 4.0 | NA | NA | 0.9 | 2541 | NA |
| p.o. (a) | 8.0 | 26.43 | 2.0 | 1.6 | 123 | 2.4 |
| p.o. (b) | 10.6 | 102.57 | 2.8 | 3.3 | 442 | 6.6 |
| p.o. (c) | 10.6 | 108.39 | 3.5 | 1.4 | 520 | 7.7 |

The oral bioavailability was lower for the hydrophilic formulation (a) than for the particle-forming compositions (b) and (c). These data suggest that bioavailability in rats may be improved significantly, i.e., more than 300%, by using the particle-forming composition of the invention.

Bioavailability in Dogs

Bioavailability of two liquid compound IIa-12 formulations was determined in fasted beagle dogs. Using a crossover study design, two separate formulations, formulations 16 and 18 from Table 1 were administered to a group of six dogs. An intravenous dose was included as the third formulation in the crossover design. Each dog received a 10 mg dose of compound IIa-12. The plasma concentrations, as determined by HPLC with fluorescence detection, were normalized to a 1 mg/kg dose. Pharmacokinetic parameters, including peak plasma concentration ($C_{max}$), time to peak plasma concentration ($T_{max}$), apparent elimination half life ($t_{1/2}$), area under the curve ($AUC_{oo}$) and the absolute bioavailability (F %) were determined.

The plasma concentration time profile of compound IIa-12 following a 1 mg/kg intravenous dose was fitted to a two compartment open model with apparent volume of distribution values of 0.96 L/kg (range 0.70-1.43 L/kg) and 1.35 L/kg (range 0.69-202 L/kg) for $V_c$ and $V_\beta$, respectively. Plasma concentrations declined with a terminal elimination half-life of 1.16 hours (range 0.89-1.38 hours). The plasma clearance of compound IIa-12 following a 1 mg/kg bolus intravenous dose in dog was 0.79 L/hr·kg (range 0.40-1.08 L/hr·kg).

Compound IIa-12 was rapidly absorbed from both of the liquid formulations with peak concentrations recorded within two hours of dosing. Peak plasma concentrations averaged 269±175 ng/ml (range 94-469 ng/ml) and 219±143 n/ml (range 96-458 ng/ml) for the Tween/propylene carbonate/PG and Tween/PG formulations, respectively. The absolute bioavailability for the two formulations was very similar, averaging 41.6±8.4 and 39.3±11.3 percent, respectively.

A separate bioavailability study involving Compound IIa-12 formulated in non-aqueous, particle forming compositions was carried out using dogs. Pharmacokinetic parameters were measured following oral dosing of eight separate formulations. Dosage was 50 mg of Compound IIa-12 per dog per day. Each formulation was evaluated in a group of three dogs, using a parallel study design.

Beagle dogs weighing 7.9-14.2 kg were used in the study. The dogs were fasted overnight prior to dosing, but were permitted water ad libitum. Food was returned to the animals at the completion of the study.

Each formulation (capsule or liquid) was administered to a group of three dogs, in a dose of 50 mg. The formulations were as described in Table 4, below. Formulations C and D are not particle-forming compositions.

TABLE 4

Formulations in Dog Study

| Form | Component (category) | Component (specific) | Amount | Solid/Liq. (room temp) |
|---|---|---|---|---|
| A | indolocarbazole | Compound IIa-12 | 25 mg/ml | semi-solid |
|   | organic solvent | propylene glycol | 40% | w/out |
|   | surfactant | Gelucire® | 60% | capsule |
| B | indolocarbazole | Compound IIa-12 | 25 mg/ml | semi-solid |
|   | organic solvent | propylene glycol | 40% | in capsule |
|   | surfactant | Gelucire® | 60% |  |
| C | indolocarbazole | Compound IIa-12 | 50 mg/ml | solid in |
|   | other | croscarmellose | 5 mg | capsule |
|   | surfactant | SDS | 5 mg |  |
| D | indolocarbazole | Compound IIa-12 | 50 mg/ml | solid in |
|   | organic solvent | PEG 1000 | 70% | capsule |
|   | organic solvent | sorbitol | 21% |  |
|   | water | water | 9% |  |
| E | indolocarbazole | Compound IIa-12 | 25 mg/ml | liquid |
|   | organic solvent | propylene glycol | 30% |  |
|   | surfactant | Captex® 200 | 14% |  |
|   | surfactant | Capmul® MCM | 11% |  |
|   | surfactant | polysorbate 80 | 45% |  |
| F | indolocarbazole | Compound IIa-12 | 25 mg/ml | liquid |
|   | organic solvent | propylene glycol | 30% |  |
|   | lipid | Captex® 200 | 14% |  |
|   | surfactant | Centrolene A | 11% |  |
|   | surfactant | polysorbate 80 | 45% |  |
| G | indolocarbazole | Compound IIa-12 | 25 mg/ml | liquid |
|   | organic solvent | propylene glycol | 30% |  |
|   | surfactant | Captex® 200 | 14% |  |
|   | surfactant | Imwitor® 308 | 11% |  |
|   | surfactant | polysorbate 80 | 45% |  |
| H | indolocarbazole | Compound IIa-12 | 25 mg/ml | liquid |
|   | organic solvent | propylene glycol | 50% |  |
|   | surfactant | polysorbate 80 | 50% |  |
| I | indolocarbazole | Compound IIa-12 | 25 mg/ml | solid |
|   | organic solvent | propylene glycol | 10% |  |
|   | surfactant | polyoxyl 40 stearate | 90% |  |
| J | indolocarbazole | Compound IIa-12 | 25 mg/ml | liquid |
|   | organic solvent | propylene glycol | 10% |  |
|   | surfactant | polyoxyl 35 castor oil | 90% |  |
| K | indolocarbazole | Compound IIa-12 | 25 mg/ml | solid |
|   | organic solvent | polyethylene glycol 1450 | 70% |  |
|   | surfactant | poloxamer 188 | 30% |  |
| L | indolocarbazole | Compound IIa-12 | 25 mg/ml | solid |
|   | organic solvent | polyethylene glycol 400 | 50% |  |
|   | surfactant | polyoxyl 40 stearate | 50% |  |
| M | indolocarbazole | Compound IIa-12 | 25 mg/ml | liquid |
|   | organic solvent | propylene glycol | 50% |  |
|   | surfactant | polysorbate 80 | 50% |  |

The reference formulation and Formulations A-C were administered during the first week of the study. Formulations D-G were administered following a one-week wash-out period. The liquid formulations A, E, F, and G were thoroughly mixed prior to dosing. Each liquid dose (2 ml) was placed in a syringe and squirted into the back of the throat of each dog and followed by about 10 ml water. A similar amount of water was administered to each dog receiving a capsule formulation.

Sequential heparinized blood samples were obtained from the jugular vein of each dog prior to dosing and at 0.25, 0.5, 1.0, 1.5, 2, 3, 4, 6, 9, and 15 hours after administration of each formulation. The blood samples were promptly chilled in an ice bath. Within two hours of collection, the samples were centrifuged (2500 rpm for 10 min.), and the plasma was transferred to polypropylene tubes and frozen at −20° C. for later analysis.

Plasma levels of Compound IIa-12 were determined by HPLC, as described below. The plasma concentration in each sample was calculated by least squares linear regression analysis (unweighted) of the peak area ratio (parent/internal standard) of the spiked dog plasma standards versus concentration. Plasma concentrations were normalized to a 5 mg/kg dose.

The mean values (±SD, N=3) for the pharmacokinetic parameters are summarized in Table 5, below. In Table 5, $C_{max}$ is peak plasma concentration; $T_{max}$ is time to peak plasma concentration; $T_{t/2}$ is apparent elimination half-life; $AUC_{0-4}$ is area under the curve (plasma conc. vs. time); and % Formulation H is relative bioavailability.

TABLE 5

Pharmacokinetic Data Summary

| Form. | $C_{max}$ ng/mL | $T_{max}$ hr | $T_{t/2}$ hr | $AUC_{0-4}$ ng · hr/mL | % of Formulation H |
|---|---|---|---|---|---|
| A | 1935.8 ± 455.7 | 1.5 | 0.83 | 5860.0 ± 1062.5 | 80.3 |
| B | 2468.1 ± 766.0 | 0.5 | — | 7608.8 ± 3267.4 | 104.2 |
| C | 11.2 ± 6.0 | 2.3 | 1.94 | 46.8 ± 25.0 | 0.6 |
| D | 940.9 ± 501.9 | 2.0 | 1.15 | 2964.3 ± 1851.6 | 40.6 |
| E | 784.6 ± 1010.3 | 1.3 | 1.07 | 2204.2 ± 2804.4 | 30.2 |
| F | 2260.6 ± 690.7 | 1.5 | 0.90 | 4761.4 ± 4465.4 | 88.9 |
| G | 1746.4 ± 1820.5 | 1.7 | 1.19 | 6491 ± 1766.3 | 64.0 |
| H | 2736.2 ± 2154.1 | 1.0 | 1.14 | 7299.8 ± 4395.4 | 100 |
| I | 1045 ± 420.5 | 1.6 | 1.1 | 3590.0 ± 1468 | 89.7 |
| J | 608.5 ± 466.5 | 1.8 | 1.2 | 2143.2 ± 1542.7 | 53.5 |
| K | 1373.0 ± 789.4 | 1.6 | 1.1 | 4480.2 ± 2576.5 | 111.9 |
| L | 1138.8 ± 609.2 | 1.9 | 1.1 | 3703.9 ± 1706.5 | 92.5 |
| M | 1305.0 ± 148.9 | 1.4 | 1.1 | 4004.0 ± 604.3 | 100 |

The area under the curve from 0 to t hours (last measurable plasma concentration time point) after dosing was calculated using the linear trapezoidal rule for the plasma-time profiles. The residual area extrapolated to infinity, determined as the final measured plasma concentration ($C_t$) divided by the terminal elimination rate constant, was added to $AUC_{0-t}$ to produce the total area under the curve ($AUC_{0-\infty}$). The bioavailability relative to that of formulation REF was calculated by dividing the $AUC_{0-4}$ of each formulation by that obtained for formulation REF.

The plasma concentrations of Compound IIa-12 were determined by reverse phase HPLC with fluorescence detection following liquid-liquid extraction of the samples with ethyl acetate:hexane (1:1, by vol.) at neutral pH. Following evaporation of the organic solvent, the samples were reconstituted with sequential aliquots of methanol and 0.1% trifluoroacetic acid in water (final ratio 1:1, by vol.). The parent compound and internal standard (Compound IIa-4) were separated from co-extracted plasma contaminants on a 25 cm×4.6 cm 5 µm Prodigy column. The mobile phase consisted of acetonitrile:methanol:0.01 tetramethylammonium perchlorate in 0.1% aqueous trifluoroacetic acid (45:5:55). Flow rate was 1.0 ml/min. Fluorescence detection ($\lambda_{em}$=288 nm, $\lambda_{ex}$=390 nm) was used for quantitation of the analytes. This HPLC assay for indolocarbazoles was linear over the concentration range of 0-5000 ng/ml. These data suggest that bioavailability in dogs may be improved significantly, i.e., by more than 300%, by using the particle-forming composition of the invention.

Bioavailability in Monkeys

A bioavailability study involving Compound IIa-51 formulated in non-aqueous, particle forming compositions was carried out using monkeys. Pharmacokinetic parameters were measured following intravenous (i.v.) administration and oral (p.o.) administration. The test composition consisted of four male cynomolgus monkeys. The i.v. dose was administered as a bolus, at a dosage level of 3 mg/kg. The oral doses were administered as soft gelatin capsules, at a dosage level of 10 mg/kg (2 capsules/monkey/dose). The oral formulations were as described in Table 6, below.

TABLE 6

Formulations in Monkey Study

| Formula | Component (category) | Component (specific) | Amount | Solid/Liq. (room temp.) |
|---|---|---|---|---|
| A | indolocarbazole | Compound IIa-51 | 20 mg/ml | solid |
|   | surfactant | Imwitor® 308 | 100% |  |
| B | indolocarbazole | Compound IIa-51 | 20 mg/ml | solid |
|   | surfactant | Imwitor® 308 | 70% |  |
|   | surfactant | Pluronic® F68 | 30% |  |
| C | indolocarbazole | Compound IIa-51 | 20 mg/ml | solid |
|   | surfactant | Imwitor® 308 | 70% |  |
|   | surfactant | Pluronic® F68 | 20% |  |
|   | organic solvent | propylene glycol | 10% |  |
| D | indolocarbazole | Compound IIa-51 | 20 mg/ml | solid |
|   | organic solvent | PEG1450 | 70% |  |
|   | surfactant | Pluronic® F68 | 30% |  |

The i.v. formulation was PEG 1450:Pluronic7; F68: hydroxypropyl-β-cyclodextrin:water.

Blood samples were collected at predetermined time points. Plasma levels of Compound IIa-51 were determined by reverse phase HPLC. Pharmacokinetic parameters were estimated by non-compartmental methods. The mean values for the pharmacokinetic parameters are summarized in Table 7, below. In Table 7, $C_{max}$ is peak plasma concentration; $T_{max}$ is time to peak plasma concentration; $T_{t/2}$ is apparent elimination half-life; AUC is area under the curve; and F % is absolute bioavailability.

TABLE 7

Pharmacokinetic Data Summary

| Route Form | $C_{max}$ ng/mL | $T_{max}$ hr | $T_{t/2}$ hr | $AUC_{0-4}$ ng · hr/mL | F % |
|---|---|---|---|---|---|
| i.v. | NA | NA | 3.0 | 2498.1 ± 347.6 | NA |
| p.o. A | 31.2 ± 15.1 | 4 | 4.7-7.2 | 392.8 ± 173.0 | 4.3 |
| p.o. B | 67.5 ± 8.9 | 4 | 4.7-7.2 | 613.7 ± 270.3 | 6.8 |
| p.o. C | 77.6 ± 12.4 | 4 | 4.7-7.2 | 678.6 ± 230.5 | 7.3 |
| p.o. D | 90.5 ± 25.2 | 1.3 | 4.7-7.2 | 977.3 ± 59.8 | 10.2 |

Following an i.v. dose, the mean clearance value was 1.1±0.1 L/hr/kg, and the mean volume of distribution was 4.9±0.7 L/kg. The results demonstrate that after i.v. administration, Compound IIa-51 had a large volume of distribution, rapid clearance, and moderate $T_{t/2}$. Based on oral dosing, formulation D had better bioavailability than the other formulations examined in this experiment. Compound IIa-51 was better absorbed from hydrophilic particles than from lipophilic particles, indicating a formulation-dependent absorption.

As those skilled in the art will appreciate, numerous modifications and variations of the present invention are possible in light of the above teachings. It is therefore understood that within the scope of the appended claims, the invention may be practiced otherwise than as specifically described herein, and the scope of the invention is intended to encompass all such variations.

What is claimed is:

1. A composition comprising a fused pyrrolocarbazole with the formula:

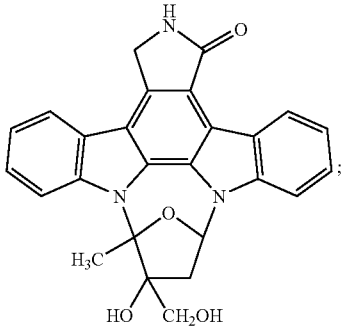

at least about 20% (w/w) of a polyoxyl stearate; and at least one polyethylene glycol.

2. The composition of claim 1 wherein the fused pyrrolocarbazole is present at a concentration of about 1 to about 100 mg/mL.

3. The composition of claim 2 wherein the fused pyrrolocarbazole is present at a concentration of about 1 to about 50 mg/mL.

4. The composition of claim 1 wherein the polyethylene glycol has a molecular weight from about 300 to about 8000 Daltons.

5. The composition of claim 4 wherein the polyethylene glycol has a molecular weight from about 400 to about 3350 Daltons.

6. The composition of claim 5 wherein the polyethylene glycol has a molecular weight from about 400 to about 1500 Daltons.

7. The composition of claim 1 wherein the polyethylene glycol is selected from PEG-400, PEG-600, PEG-1000, and PEG-1450.

8. The composition of claim 7 wherein the ratio of polyethylene glycol:polyoxyl stearate ranges from about 50:50 to about 80:20.

9. The composition of claim 8 wherein the ratio of polyethylene glycol:polyoxyl stearate is about 50:50.

10. The composition of claim 8 wherein the ratio of polyethylene glycol:polyoxyl stearate is about 80:20.

11. The composition of claim 1 comprising a polyethylene glycol mixture selected from PEG-400/PEG-1000, PEG-400/PEG-1450, PEG-600/PEG-1000, and PEG-600/PEG-1450.

12. The composition of claim 11 wherein the ratio of the polyethylene glycol mixture:polyoxyl stearate is from about 50:50 to about 80:20.

13. The composition of claim 12 wherein the ratio of the polyethylene glycol mixture:polyoxyl stearate is about 50:50.

14. The composition of claim 12 wherein the ratio of the polyethylene glycol mixture:polyoxyl stearate is about 80:20.

15. The composition of claim 13 wherein the composition comprises PEG-400:PEG-1000:polyoxyl stearate in a ratio of about 25:25:50.

16. The composition of claim 13 wherein the composition comprises PEG-400:PEG-1450:polyoxyl stearate in a ratio of about 25:25:50.

17. The composition of claim 14 wherein the composition comprises PEG-400:PEG-1000:polyoxyl stearate in a ratio of about 40:40:20.

18. The composition of claim 14 wherein the composition comprises PEG-400:PEG-1450:polyoxyl stearate in a ratio of about 40:40:20.

19. The composition of claim 7 wherein the polyoxyl stearate is polyoxyethylene (40) stearate.

20. The composition of claim 12 wherein the polyoxyl stearate is polyoxyethylene (40) stearate.

21. A method of treating of acute myelogenous leukemia comprising administering a composition according to claim 1 to a subject in need thereof.

* * * * *